United States Patent [19]
Mandecki

[11] Patent Number: 5,981,166
[45] Date of Patent: *Nov. 9, 1999

[54] SCREENING OF SOLUBLE CHEMICAL COMPOUNDS FOR THEIR PHARMACOLOGICAL PROPERTIES UTILIZING TRANSPONDERS

[75] Inventor: Wlodek Mandecki, Edison, N.J.

[73] Assignee: Pharmaseq, Inc., Monmouth Junction, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/842,383

[22] Filed: Apr. 23, 1997

[51] Int. Cl.[6] .............................. C12Q 1/00; C12Q 1/42; C12Q 1/18; G01N 33/53
[52] U.S. Cl. .................. 435/4; 435/21; 435/968; 435/32; 435/28; 422/82.01; 342/42; 204/157.15
[58] Field of Search .................. 435/4, 21, 968, 435/32, 28; 422/82.01; 342/42; 204/157.15

[56] References Cited

U.S. PATENT DOCUMENTS

| | | | |
|---|---|---|---|
| 4,177,253 | 12/1979 | Davies et al. | 435/4 |
| 4,297,337 | 10/1981 | Mansfield et al. | 435/4 |
| 4,452,773 | 6/1984 | Molday | 435/4 |
| 4,454,234 | 6/1984 | Czerlinski | 435/4 |
| 4,556,883 | 12/1985 | Strietzel | 435/4 |
| 4,672,040 | 6/1987 | Josephson | 435/4 |
| 4,777,145 | 10/1988 | Luotola et al. | 435/4 |
| 4,778,769 | 10/1988 | Forrest et al. | 435/4 |
| 4,822,566 | 4/1989 | Newman | 435/4 |
| 4,857,893 | 8/1989 | Carroll | 435/4 |
| 4,923,819 | 5/1990 | Fernandez et al. | 435/4 |
| 4,941,201 | 7/1990 | Davis | 435/4 |
| 4,965,188 | 10/1990 | Mullis et al. | 435/4 |
| 5,019,815 | 5/1991 | Lemelson et al. | 435/4 |
| 5,034,192 | 7/1991 | Wrighton et al. | 435/4 |
| 5,071,774 | 12/1991 | Vorpahl et al. | 435/4 |

(List continued on next page.)

FOREIGN PATENT DOCUMENTS

| | | |
|---|---|---|
| 0526173 A2 | 2/1993 | European Pat. Off. |
| WO90/13666 | 11/1990 | WIPO |
| WO93/04199 | 3/1993 | WIPO |
| WO93/21340 | 10/1993 | WIPO |
| 9636436 | 11/1996 | WIPO |
| WO96/36436 | 11/1996 | WIPO |
| 9719958 | 6/1997 | WIPO |
| WO97/19958 | 6/1997 | WIPO |
| WO97/20073 | 6/1997 | WIPO |
| WO97/20074 | 6/1997 | WIPO |

OTHER PUBLICATIONS

Albretsen, C et al. "Applications of magnetic beads with covalently attached oligonucleotides in hybridization: Isolation and detection of specific measles virus mRNA from a crude cell lysate" *Analytical Biochemistry* (1990) vol. 189, pp. 40–50.

Alper, J. "Drug Discovery on the assembly line" *Science* (Jun. 3, 1994) vol. 264, pp. 1399–1401.

Atkinson, T et al. "A convenient procedure for the synthesis of oligodeoxyribonucleotide affinity columns for the isolation of mRNA" *Nucleic Acids Research*, (1988), vol. 16, No. 13.

Cargill, JF and BE Toyonaga. *The Chemical Factory: An Assembly Line Approach to Automated Combinatorial Chemistry on Solid Phase* (1994).

Caruthers, MH et al. "Deoxyoligonucleotide synthesis via the phosphoramidite method" *Gene Amplification and Analysis*, vol. III, (TS Papas et al., eds.) Elsevier Press, Amsterdam (1995).

(List continued on next page.)

*Primary Examiner*—Louise N. Leary
*Attorney, Agent, or Firm*—Brinks Hofer Gilson & Lione

[57] ABSTRACT

The invention provides a method to rapidly screen chemical compounds by delivering the compounds to the assay as a coating on transponders, rather than as powder or solution. The transponder's function is to store data that identify the compound. The data can be decoded in any moment of the assay, and the identity of the desired compound established.

10 Claims, 3 Drawing Sheets

U.S. PATENT DOCUMENTS

| | | | |
|---|---|---|---|
| 5,153,583 | 10/1992 | Murdoch | 435/4 |
| 5,200,051 | 4/1993 | Cozzette et al. | 435/4 |
| 5,202,231 | 4/1993 | Drmanac et al. | 435/4 |
| 5,214,409 | 5/1993 | Beigel | 435/4 |
| 5,218,343 | 6/1993 | Stobbe et al. | 435/4 |
| 5,223,851 | 6/1993 | Hadden et al. | 435/4 |
| 5,235,326 | 8/1993 | Beigel et al. | 435/4 |
| 5,245,332 | 9/1993 | Katzenstein | 435/4 |
| 5,250,944 | 10/1993 | Urbas et al. | 435/4 |
| 5,252,962 | 10/1993 | Urbas et al. | 435/4 |
| 5,257,011 | 10/1993 | Beigel | 435/4 |
| 5,262,772 | 11/1993 | Urbas et al. | 435/4 |
| 5,266,926 | 11/1993 | Beigel | 435/4 |
| 5,284,748 | 2/1994 | Mroczkowski et al. | 435/4 |
| 5,347,263 | 9/1994 | Carroll et al. | 435/4 |
| 5,422,636 | 6/1995 | Urbas et al. | 435/4 |
| 5,440,300 | 8/1995 | Spillman, Jr. | 435/4 |
| 5,445,970 | 8/1995 | Rohr | 435/4 |
| 5,466,348 | 11/1995 | Holm-Kennedy | 435/4 |
| 5,481,262 | 1/1996 | Urbas et al. | 435/4 |
| 5,491,097 | 2/1996 | Ribi et al. | 435/4 |
| 5,492,806 | 2/1996 | Drmanac et al. | 435/4 |
| 5,525,464 | 6/1996 | Drmanac et al. | 435/4 |
| 5,552,270 | 9/1996 | Khrapko | 435/4 |
| 5,641,634 | 6/1997 | Mandecki | 435/4 |
| 5,736,332 | 4/1998 | Mandecki | 435/4 |

U.S. PATENT DOCUMENTS

Drmanac, R et al. "DNA sequence determination by hybridization: a strategy for efficient largescale sequencing." *Science* (1993) vol. 260, pp. 1649–1652.

Fiore, F et al. "The Abbott IMx Automated Benchtop Immunochemistry Analyzer System" *Clinical Chemistry* (1998) vol. 34, No. 9.

Ghosh, SS and GF Musso. "Covalent attachment of oligonucleotides to solid supports" *Nucleic Acids Research*, (1987) vol.15, No. 13.

Gingeras TR et al. "Hybridization properties of immobolized nucleic acids" *Nucleic Acids Research* (1987) vol. 15, No. 13.

Hooft van Hujisduijnen, RAM et al. "A means to reduce the complexity of oligonucleotides encoding degenerate peptides" *Nucleic Acids Research* (1992) vol. 20, No. 4.

Hultman et al. "Direct solid phase sequencing of genomic DNA using magnetic beads as solid support" *Nucleic Acids Research* (1989) vol. 17, No. 13, pp. 4937–4946.

Ihalainen et al. *Biotechniques* (1994) vol. 16, pp. 938–943.

Kurstak, E. *Enzyme Immunodiagnostics* (1986) pp. 13–22, Academic Press, NY.

Lam, KS et al. "A new type of synthetic peptide library for identifying ligand–binding activity" *Nature* (Nov. 7, 1991) vol. 354, pp. 82–84.

Maskos, E. et al. "Oligonucleotide hybridisations [sic] on glass supports: a novel linker for oligonucleotide synthesis and hybridisation [sic] properties of oligonucleotides synthesized in situ" *Nucleic Acids Research* (1992) vol. 20, No. 7, pp.1679–1684.

McHugh, T. "Flow Microsphere Immunoassay for the Quantitative and Simultaneous Detection of Multiple Soluble Analytes" *Methods in Cell Biology* (1990) vol. 42, pp. 575–595.

Mirzabekov, AD. "DNA sequencing by hybridization—a megasequencing method and a diagnostic tool" *Tibtech* (1994) vol. 12.

Moran et al. "Radio frequency tag encoded combinatorial library method for the discovery of tripeptide–substituted cinnamic acid inhibitors of the protein tyrosine phosphatase PTP1B" *J. Am. Chem Soc.* (1995) vol. 117, pp. 10787–10788.

Morrissey, NE et al. "Modified method for determining carcinoembryonic antigen in the presence of human anti–murine antibodies" *Clinical Chemistry* (1993) vol. 39, No. 3.

Nicolaou et al. "Radiofrequency encoded combinatorial chemistry" *Angew. Chem Int. Ed.* (1995), vol. 34, No. 210, pp. 2289–2291.

Pease, AC et al. "Light–generated oligonucleotide arrays for rapid DNA sequence analysis" *Proc. Natl. Acad. Sci.* (1994), vol. 91, pp. 5022–5026.

Pierce catalog. (1994) pp. T159, T1314–T315, Rockford, Illinois US.

*Principles And Practice Of Immunoassay*, Chapter 5, "Immunoassay Design And Optimization". (1994).

*Principles And Practice Of Immunoassay*, Chapter 13, "Heterogeneous Fluoroimmunoassay." (1995).

Sambrook et al. *Molecular Cloning: A laboratory manual* (1989) $2^{nd}$ ed. Lakes Press, NY.

Service, R. "Radio tags speed compound synthesis" *Science*, (Oct. 27, 1995) vol. 270, page 577.

Sproat, BS and DM Brown "A new linkage for solid phase synthesis of oligodeoxyribonucleotides" *Nucleic Acids Research* (1985) vol. 13, pp. 2979–2987.

Urdea et al. "A comparison of non–radioisotopic hybridization assay methods using flourescent, chemiluminescent and enzyme labeled synthetic oligodeoxyribonucleotide probes" *Nucleic Acids Research*, (1988) vol. 16, No. 11 pp. 4937–4956.

Panel A:

Panel B:

Panel C:

+

C*

Panel D:

SCREENING OF SOLUBLE CHEMICAL COMPOUNDS FOR THEIR PHARMACOLOGICAL PROPERTIES UTILIZING TRANSPONDERS

BACKGROUND OF THE INVENTION

This invention relates to materials and methods for screening chemical compounds for potential pharmaceutical activity, and more specifically to an assay for soluble compounds, wherein the compounds are delivered to the assay in a form of a coating on solid phase particles carrying microtransponders. The coating is dissolved and the compounds are released just prior to or during the assay, and the identity of the compound is provided by the serial number encoded on the transponder.

Libraries of chemical compounds in possession of large pharmaceutical companies have more than 100,000 individual compounds. The advent of combinatorial chemistry for the synthesis of compound has accelerated the growth of the number of compounds in libraries. It is anticipated that within a few years the size of the largest libraries of individual chemical compounds will approach or even exceed $10^6$.

The number of macromolecular targets of interest, such as receptors, enzymes or proteins, is rapidly growing as well, due to the progress with rapid methods to sequence genes, to classify the genes and proteins, to predict the structure of proteins, and to analyze their function. The human genome project is a significant factor contributing to the rapid growth of the number of targets of interest.

The growth of the number of chemical compounds and the number of targets create a need for rapid methods to analyze the properties of the compounds from chemical libraries with respect to the macromolecular targets. The methods currently being used rely on robotics and automation to dispense, dissolve, aliquot, mix and analyze the compounds. The automated systems are complex due to the number of vessels and transfer steps.

The subject of this invention is a method to tag soluble chemical compounds to minimize the number of handling steps and the complexity of handling the compounds, and to reduce the time needed for the analysis of the library. The above improvements will also enable small laboratories which do not have the sophisticated automated systems to perform the screening, since according to the present invention, inexpensive and readily available instrumentation should suffice.

In a preferred implementation of this invention, a transponder is used as a carrier for the drug. A transponder is a radio transmitter-receiver activated for transmission of data by reception of a predetermined signal, and may also be referred to as a microtransponder, radiotransponder, radio tag, transceiver, etc. The signal comes from a dedicated scanner, which also receives and processes the data sent by the transponder in response to the signal. The scanner function can be combined with the write function, i.e. the process of encoding the data on the transponder. Such a combination instrument is called a scanner read/write device. An advantage of the transponder-scanner system stems from the fact the two units are not physically connected by wire, but are coupled inductively, i.e. by the use of electromagnetic radiation, typically in the range from 5–1,000 kHz, but also up to 1 GHz and higher.

Several transponders currently available commercially have been described in four previous patent applications, Case No. 7295/4, 7295/5, 7295/9, 7295/10 (Brinks Hofer Gilson & Lione, Chicago). They include Bio Medic Data Systems' (BMDS, 255 West Spring Valley Ave., Maywood, N.J.) programmable transponder for use in laboratory animal identification. The transponder is implanted in the body of an animal, such as a mouse, and is glass-encapsulated to protect the electronics inside the transponder from the environment. One of the transponders manufactured by this corporation, model# IPTT-100, has dimensions of 14×2.2× 2.2 mm and weighs 120 mg. The transponder is user-programmable with up to 16 alphanumeric characters, the 16th letter programmable independently of the other 15 letters, and has a built-in temperature sensor as well. The electronic animal monitoring system (ELAMS) includes also a scanner read/write system to encode or read data on/from the transponder. The construction of the transponder and scanner is described in U.S. Pat. Nos. 5,250,944, 5,252,962 and 5,262,772, the disclosures of which are incorporated herein by reference. Other similar transponder-scanner systems include a multi-memory electronic identification tag (U.S. Pat. No. 5,257,011) manufactured by AVID Corporation (Norco, Calif.) and a system made by TEMIC-Telefunken (Eching, Germany). AVID's transponder has dimensions of 1 mm×1 mm×11 mm, and can encode 96 bits of information, programmed by the user. The present invention can be practiced with different transponders, which might be of different dimensions and have different electronic memory capacity.

Transponders of the type discussed above have been disclosed for use in drug discovery by Mandecki (see patent applications listed above) and have been used for solid phase synthesis of compounds followed by screening in an assay for a pharmaceutically relevant biological activity (Moran, E. J. et al. 1995, Radio frequency tag encoded combinatorial library method for the discovery of tripeptide-substituted cinnamic acid inhibitors of the protein tyrosine phosphatase PTB1B. *J. Am. Chem.* Soc. 117, 10787–10788; Service, R. F. 1995, Radio tags speed compound synthesis (an editorial). *Science* 270, p. 577). In both of these applications the compounds were covalently and permanently linked to the transponders. According to the present invention, the compounds are only deposited (coated) on the surface of the transponders, and can undergo a dissolution under very mild conditions (simple exposure to buffers will suffice) without any changes of the chemical structure of the compounds. When dissolved, the compounds can be tested in assay configurations commonly used for testing soluble compounds.

SUMMARY OF THE INVENTION

The invention is an improvement to a bioassay for soluble compounds. The invention involves the coating of the transponder with a polymer layer that contains the desired chemical compound. The transponder is also electronically encoded with a serial number that identifies the compound. To assay the compound, the coated transponder is immersed in a buffer in a vessel (e.g. test tube or a well of a microtiter plate). The buffer composition is adjusted such that (1) the coating of the transponder can be promptly dissolved and the chemical compound of interest brought into solution, and (2) the assay can be performed in the same solution. The receptor is added to the vessel, and the assay performed using essentially the same steps which would be used in the assay configured for the soluble chemical compound.

The coating of transponders is done individually for different soluble compounds in the chemical library. Different compounds are assigned different identification numbers encoded on the transponders. The act of decoding the transponder unmistakably identifies one compound out of a set of compounds. Chemical libraries of different sizes, from 10 compounds to millions of compounds and more, can benefit from the invention.

In the last step of the assay, the vessels which are considered positive as a result of the desired interaction of the compound with the receptor are identified. The transponders are removed from the vessels, and electronically decoded. The decoding gives the identification number of the compound, and this number is then used to positively identify the compound. The compound(s) is subjected to further biochemical testing.

The invention is also a new method for storage of chemical compounds. Rather than traditionally storing the compounds as powder, liquid or solids, the compound is stored as a coating on the transponder. The benefit is that different compounds in the above new form (i.e. coated on the transponder) can be mixed and moved from one vessel to another without loosing the track for the identity of the compounds. It is envisioned the full library of 100,000 chemical compounds could be stored in the form of 100,000 transponders, and if the transponder size is 0.3 mm×0.3 mm×0.3 mm, the volume of the container would be only about 3 ml, assuming that each compound is represented by one coated transponder and the transponders are tightly packed.

The invention is also a method for dispensing of chemical compounds. Rather than weighing out the compound, a coated transponder is provided.

The invention is a new type of the delivery of soluble chemical compounds to the assay, the delivery being in the form of the solid phase particle, coated by the compound, the core of the solid phase particle being the transponder, which stores the information that allows to identify the compound.

The transponder carrying the soluble chemical compound is analogous to a tablet having the electronic core. Tablets, defined in pharmaceutical sciences as solid dosage forms containing drug substances, have been in widespread use since the second half of the 19th century (although they have not carried the electronic core). There have been a great variety of methods to prepare tables, as described in the references cited below. They are divided into two general classes, whether they are made by compression or molding. Compressed tablets are formed by compression from powdered, crystalline or granular materials. They include sugar-coated tablets, film-coated tablets, enteric-coated tablets, multiple compressed tablets (layered or press-coated), controlled-release tablets, tablets for solution, effervescent tablets, compressed suppositories or inserts and buccal or sublingual tablets. Molded tablets are made from moist material using a triturate mold. They include dispensing tablets and hypodermic tablets.

Many of the methods to prepare tablets can be used to practice the present invention. The essential requirements are that the chemical compound is physically associated with the transponder core and that the compound can be dissolved passively in the buffer suitable for the assay.

DETAILED DESCRIPTION OF THE INVENTION

The critical aspect of the present invention is the association of the chemical compound with the tag (e.g., a transponder) that does not change the chemical nature of the compound and does not involve the formation of a covalent bond between the compound and the solid support. Many types of the association are applicable. The drug may be present as a constituent of a coating on the transponder, or it can be in a form of a small tablet or a particle(s) attached or glued to the transponder. The drug can also be trapped inside the transponder, or it can be placed inside a capsule together with a transponder. Many other types of association are feasible.

Figure 1:
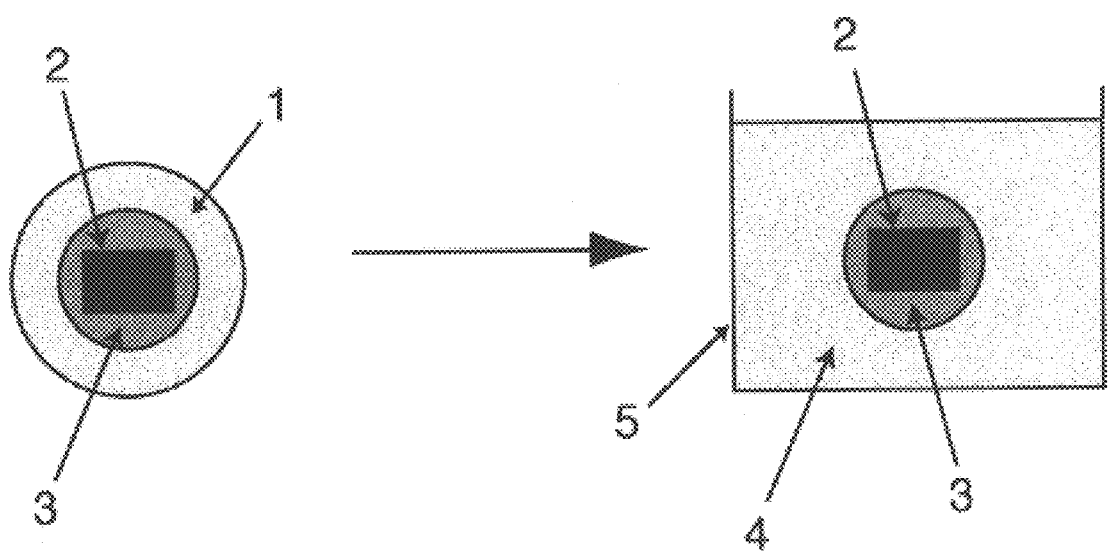
FIG. 1 highlights the principle of the invention, showing how the drug coated on the solid phase tag (transponder) is dissolved in the assay.

FIG. 1 demonstrates the principle of the invention. The drug is present as a constituent of a coating 1 on a solid phase particle 3 comprising the transponder 2. The solid phase particle 3 is moved to a vessel 5 and immersed in a dissolution medium 4 present in the vessel. The coating undergoes a spontaneous dissolution, and the drug is dissolved in the medium. The rate of the dissolution process can be controlled by adjusting the composition of the coating or the dissolution medium, as well as adjusting temperature, agitation, or possibly many other parameters.

Many types of encoding can be used to practice the present invention. The preferred encoding involves using of the transponders, each being encoded with a serial number. The communication with the transponder relies upon the transmission of the signal by electromagnetic radiation, such signal being received by a dedicated RF scanner. The types of transponders that have been used in the biomedical field include the models which are interrogated by radio frequency electromagnetic radiation. A preferred type of transponder is the miniature laser light induced transponder, due to its small dimensions and low manufacturing cost.

Alternative types of encoding include any other means of storing information on a solid phase particle. One method involves writing a serial number in a repetitive fashion on an object (such as silicon substrate) by etching, the etching being done by e.g. photolithography (similar to that used to manufacture electronic integrated circuits). The object is then cut to form small solid phase particle, each or most of which will carry a serial number. The number can be etched in a form of a standard decimal number, or as a string of any type of characters, according to principles established before the printing, or in a form of a bar code, or in any other coded form. An alternative to etching might be microprinting or ink-jetting on a flat and thin object, which is subsequently cut to yield small solid phase particles. Yet another method involves holographic encoding of an image of serial number, either in a direct (decimal) form or in any encoded form. The property of a holographic image is that small fractions of the holographic picture retain much of the information of the whole picture, meaning that small solid phase particles that carry fractions of the image, will carry sufficient information to obtain the serial number of the solid phase particle. Different means of storing information will require different types of readers, such as optical character recognition system, bar code reader, etc.

The paragraphs below give a description of the preferred mode of storing the serial number in a small solid phase particle.

Design of the Laser-Induced Transponder

Figure 2:
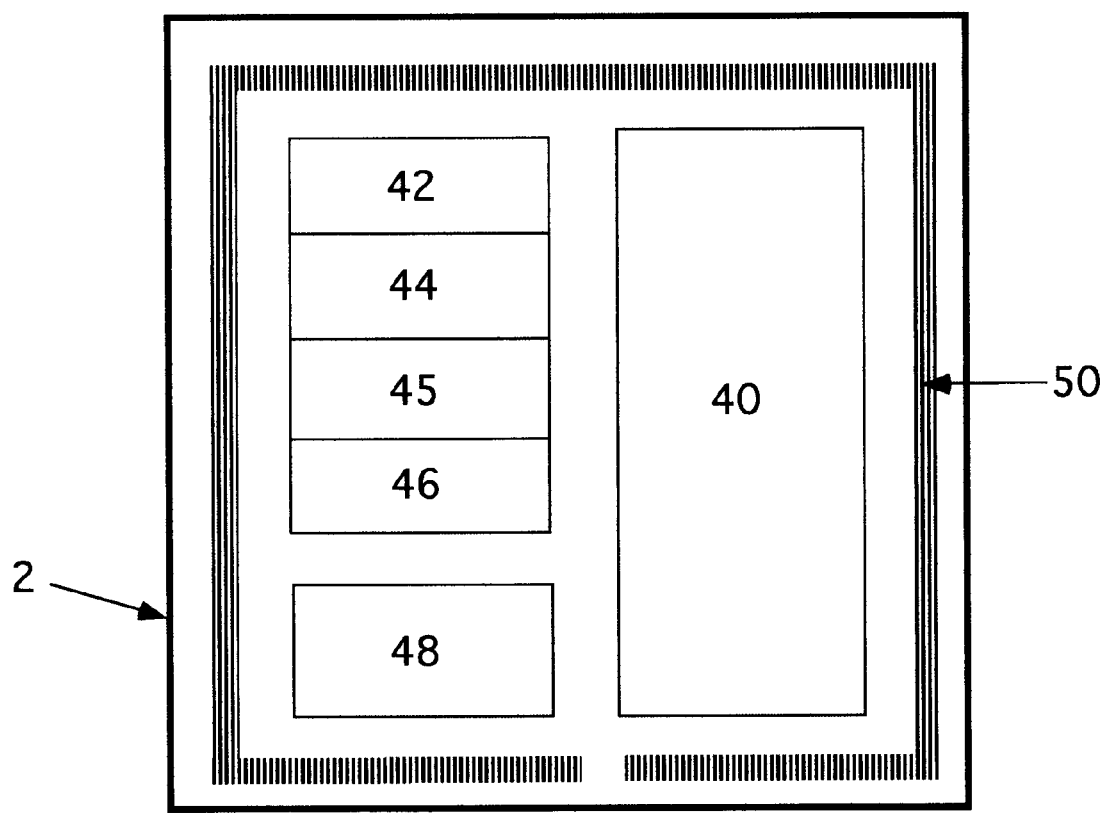
FIG. 2 is a schematic representation of a miniature transponder.

FIG. 2. depicts the design of the radio-frequency (RF) laser light induced transponder, which is a monolithic integrated circuit (IC), i.e. a single chip. The preferred size of the transponder 2 is from 0.5 mm long×0.5 mm wide×0.5 mm thick, down to 0.25 mm×0.25 mm×0.25 mm, or possibly even smaller. The thickness is equal to the thickness of the silicon substrate used to manufacture the wafer. The power for the transponder is provided by a photovoltaic cell array 40. Most of the power generated will be used to energize the onboard oscillator 48. The purpose of the oscillator is to transmit the data encoded in the transponder (the serial number) to the receiver by radio waves. The transmission frequency will be in the range of a few hundred megahertz. The signal from the oscillator will be received by a highly sensitive RF receiver.

The IC will contain programmable ROM 42 for encoding of the serial number. The program bits are laser programmed. The preferred size of the ROM is from 10 bits, allowing for $2^{10}=1,024$ different index numbers for the transponders, up to 50 bits, allowing for $10^{15}$ different serial numbers and assuring that all transponders manufactured may have different serial numbers.

The oscillator ring will be spread around the outside perimeter of the IC to give the resulting antenna as much cross section as possible, while the core of the IC will contain the photocells, the logic, and the program bits.

The logic will perform the function of sending a preamble followed by the programmed bit sequence. The preamble will be used by the receiver to detect the baud rate. This is analogous to how the bar code scanner detects the correct code patterns independent of the speed that the bar code is moved passed the detector.

The source of the electrical power for the transponder is at least one photovoltaic cell within the transponder and can be illuminated by a laser. The same light also induces the fluorescence of fluorogenic molecules immobilized on the surface of the transponder. The contents of the ROM memory is converted from the digital form to the analog form by a Digital-to-Analog converter 44 mounted on the transponder. The signal is amplified by an amplifier 45, mixed with the carrier signal produced by an oscillator 48, and emitted to the outside of the transponder by an antenna 50.

Many different transponder designs are feasible, including but not limited to the transponders having the user programmable memory. A user programmable transponder carries an additional Analog-to-Digital converter 46.

The advantages of the proposed transponder design over commercially available transponders are several-fold. First, the transponder dimensions are greatly reduced relative to a conventional transponder, because most of the volume of a conventional transponder is occupied by the solenoid. The design discussed above enables the production of cube-shaped transponders measuring 0.25 mm on the side, or less. This dimension is related to the current practical minimum for the thickness of the silicon wafer.

Second, a large number of transponders can be manufactured on a single silicon wafer that is simply cut by laser to yield active transponders. Third, the transponder, according the new design, will not need the glass capsule as an enclosure, further reducing the size of the transponder. Silicone dioxide ($SiO_2$) would constitute a significant portion of the surface of the transponder; the $SiO_2$ has chemical properties of glass with respect to the derivatization or immobilization of biomolecules. Alternatively, the transponder may be coated with a variety of materials, including plastic, latex and the like.

Finally and most importantly, the narrow focus of the beam of laser light would enable only one transponder to be active at a time during the decoding step, significantly reducing noise level, if many transponders are decoded at a time.

Coating Procedure

The preferred coating procedure is the one which is applicable to three classes of drugs, basic, neutral or acidic. An example of a basic drug is tenormin (beta adenergic blocker, also known as atenolol), manufactured by Imperial Chemical Industries. Another example of a basic drug is timolol maleate, also a beta adenergic receptor, made by Merck Sharp and Dohme. An example of a neutral compound is keflex, an antibiotic and an amino acid, manufactured by Eli-Lilly). Aspirin (acetyl salicilic acid) is an example of an acidic drug. The procedure is similar to that used for manufacturing of sustained release tablets. The principle of coating relies on immersing the transponders in a solution which is the mixture of the desired drug and a polymer in an organic solvent. The transponders are incubated in the solution for an appropriate time with stirring, then removed and dried. Transient (temporary) bonds will be formed between the polymer and $SiO_2$ surface of the transponders, and the drug will be trapped in the polymer layer.

The coating procedure will easily yield the coating containing about 10 $\mu$g (the useful range being between 1 ng to 1 mg) of the drug on each transponder (0.5 mm×0.5 mm×0.5 mm). The amount of the drug in the coating can be adjusted, depending on the need and the solubility of the drug, by fine-tuning the formulation of the polymer-drug solution. The amount of the chemical compound needed to be deposited on the transponder can be calculated as follows. If the volume of the assay is 100 $\mu$l, and the desired drug concentration for the first-round screening is 10 $\mu$M (which is a fairly high concentration), then for the compound having the molecular weight $M_r=300$ daltons the amount to be deposited on the transponder is 0.3 $\mu$g. This is a minute amount that can be readily deposited as a component of the coating.

The coating can cover all of the transponder surface, or a part of the surface. The primary coating can be the final layer deposited on the transponder, or another protective layer can be deposited on the primary layer. The coating preferably contains just one chemical compound, but to increase the assay throughput, several chemical compounds can be deposited on a single transponder. In such case, the electronic decoding of the transponder identifies a group of compounds, one or more of which has a biological activity.

Assays

The essence of the present invention is a new type of the delivery of the chemical compound to a biological assay as a coating on a solid phase particle (e.g., a transponder). After the dissolution step, the compound is investigated in its soluble form, as it is the case in a great majority of current biological assays for compounds of pharmaceutical interest. Therefore, virtually any existing bioassay can benefit from the present invention. Typical bioassays involve a receptor, enzyme, any other type of a protein, nucleic acid, carbohydrate etc. as targets for the binding of the compound.

In many instances, the solubilized compound can be used directly in the assay, as it is the case in (a) an enzyme inhibition assay; (b) in vitro cell-based assay, where changes of the cellular metabolism are being observed (cell death, growth attenuation, increased synthesis of a biomolecule, or inhibition of the synthesis of a biomolecule); or (c) direct binding assay, in which the act of molecular binding itself is followed using a physico-chemical method, such as the plasmon resonance (implemented on Pharmacia's BIAcore).

Figure 3:
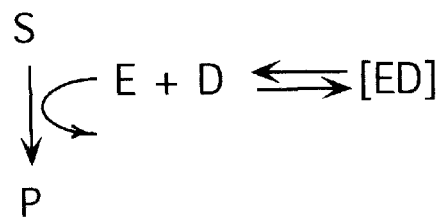
FIG. 3 is a brief presentation of the reaction schemes for some assays discussed in the text. Abbreviations: C*, competing reagent; D, drug (chemical compound); R, receptor; [], denotes a complex of two molecules given in the bracket, S, enzyme substrate; P, product of the enzymatic reaction. Panel A, assay for the inhibition of enzyme activity; Panel B, receptor-based assay; Panel C, competitive receptor-based assay; Panel D: solid-phase receptor assay based on the drug entrapment principle.
Figure 3:
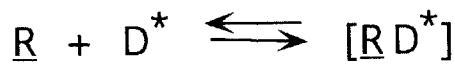
Figure 3:
Figure 3:
Figure 3:
Figure 3:

The principle of an enzyme inhibition assay is illustrated in Panel A, FIG. 3. Drug D, a constituent of the transponder's coating and subsequently dissolved and transferred to the reaction buffer, can bind and inhibit the enzyme E. The formation of the inactive drug-enzyme complex [ED] reduces the observed enzymatic activity and the rate of conversion of substrate S to product P, which concentration is measured in the assay. The low rate of accumulation of product P is an indication of the desirable activity of drug D.

In other cases, the compound might carry a reporter group (such as biotin, fluorescein, any chromogenic group, radioactive label, chemiluminescence label, etc.). Then, a direct assay can be used as well, and the activity of the reporter group associated with the target can be readily detected by measuring the reporter function.

Panel B of FIG. 3 provides a scheme of an assay in which chemical compounds conjugated to fluorescein are used. Receptor R immobilized on solid phase is exposed to compound D*. Compounds having the binding affinity for the receptor form a fluorescent complex, [RD*], also immobilized on solid support. The fluorescence of the solid phase is an indication of the compound's affinity for the receptor.

Often, the direct assay will not be feasible (e.g. if the in vitro assay is not desired or possible and the compounds do not carry a reporter group). A competitive binding assay is one method to investigate the binding of the compound in such a case. In a competitive assay, as demonstrated in Panel C of FIG. 3, a reagent C* that is known to bind to the target R is provided. Often, the reagent does not have desired pharmacological properties. The reagent is typically labeled with a reporter group (such as fluorescein), indicated in FIG. 3 by an asterisk. If the mixture of the tested compound D and the reagent-conjugate is incubated with the target, and if the compound D is able to bind to the target R forming complex [RD], then the binding of the reagent-conjugate C* will be inhibited by the compound D. As a result, a low level of activity of the reporter group associated with the receptor will be observed. The competitive assay is often solid phase-based, and the target can be immobilized on the solid phase.

A variation of the assay presented in Panel C of FIG. 3 is the fluorescence polarization assay. The competing compound C* used in the assay needs to bind to the receptor, be fluorescent and have low molecular weight to allow for observable changes of the polarization of the emitted light. The binding of the tested compound D is determined by measuring the fluorescence polarization of the mixture. Low polarization signal of the mixture being analyzed is an indication that the tested compound D binds to the target. A benefit of the fluorescence polarization assay is that the assay is done in solution (and does not involve the solid phase).

Another assay configuration is presented in Panel D of FIG. 3. This assay takes advantage of a property of surfaces coated with the mixture of the polymer and the relevant chemical compound, such property being the display of the chemical compound on the surface as a result of its entrapment in the polymer coating despite the lack of the covalent chemical bond between the compound and either the surface itself or the polymer. The receptor R* conjugated to a fluorescent hapten is allowed to bind to a solid phase particle comprising the transponder. The solid phase is coated with a mixture comprising a drug being tested D. The solid phase is exposed to a solution containing R*. Binding of the receptor R* to the drug D to form the [R*D] complex manifests itself as an increased fluorescence of the solid phase particle.

EXAMPLE 1

Coating of the Transponders with a Drug

The procedure in this example is used to coat a set of transponders with a single chemical compound. In the first step, each of the transponders in the set is passed through the RF scanner, the serial number of the transponder is read and permanently recorded in the memory of a computer. The serial numbers are associated with the name of the chemical compound used to coat the transponders. These numbers will be eventually used to determine the compound having a desired biological activity in an assay.

The surface of the transponder is prepared by washing with deionized distilled water till the pH of wash is around 7. The surface should not be contaminated with any acidic or basic material. Transponders do not need to be dried if acetone is used for coating (if the solvent is chloroform then the transponders need to be dried).

The polymer solution in acetone (reagent grade) is prepared first. There are many examples of suitable polymers. One polymer, poly-(DL)lactic acid (molecular weight of about 30,000–200,000 daltons), is used quite often. Examples of other suitable polymers are alginic acid, cellulose, polyacrylamide, acrylic acid or anhydride copolymer. It needs to be ascertained that the polymer does not interact appreciably with the drug(s).

The concentration of poly-(DL)lactic acid should be in the range of 1% to 20%, i.e. 1 to 20 grams per 100 ml of acetone. The polymer is added in a stepwise fashion to 100 ml of acetone in a 500 ml round bottom flask kept at room temperature. The solution is stirred using either magnetic or mechanical stirring with a motor until the solution is clear, typically for 15–60 min.

Next, the drug is dissolved in the solvent. The concentration of the drug, such as tenormin, should be in the range of 1% to 10%, most often it will be about 1%. Low concentrations of the drug will effectively control the deposition of the drug on the transponder's surface. Amounts higher than 10% can prevent the drug-polymer mixture from sticking to the surface. 1 g of tenormin is dissolved in 100 ml of acetone in another 500 ml round bottom flask at room temperature. Stirring can be either magnetic or mechanical. The solution is stirred until it is clear. If the drug is difficult to dissolve and the solution is not clear, it may be necessary to heat the mixture to not more than 40° C.

In the following step, the drug-polymer solution is prepared by mixing the polymer solution and the drug solution with each other. The drug solution (100 ml) is added gradually in a dropwise fashion to the polymer solution (100 ml) at room temperature. The use of a separatory funnel or another dispensing device, as well as of a slow mechanical stirring mechanisms are recommended. The final mix should not exhibit any discernible layers. A typical duration of the above mixing procedure is about 1 hour and should yield about 200 ml of the drug-polymer solution in acetone.

The transponders are coated in a 500 ml beaker. The beaker is rinsed with a very dilute (0.1–1%) solution of polymer in acetone and dried before using to prevent excess coating of the glass with the drug. Up to 10 grams of transponders is placed in the beaker, then about 20 ml of acetone is added to moisten the surface of transponder with acetone. The drug-polymer solution needs to be added in a dropwise mode over about 1 hour. The use a mechanical stirring device is recommended strongly to prevent the transponders from sticking one to another. The stirring should be slow initially (about 60–120 rpm). Then the stirring speed needs to be increased. The coating should be done at room temperature (20–27° C.). The duration of the coating may have to be determined experimentally, but it is typically between 30 min and 3 hours. The coating procedure can be monitored by using a regular microscope to examine the transponder surface.

The coated transponders need to be dried. First, the contents of the beaker moved to a 500 ml round bottom flask and the excess polymer solution is removed by decantation while stirring mechanically at all times. The flask needs to be immersed in a water bath at room temperature at all times. High vacuum (0.1–0.5 mm Hg) is applied, and the stirring continues until the solvent is not seen any more and the transponders are dry. A good indication for the dryness is the increased mobility of the transponder. It may be needed in some cases to increase the temperature of the water bath up to 30° C. The coating procedure can be repeated, up to 10 times or more, to further increase the amount of drug deposited on the surface of transponders.

The transponders need to be properly stored, preferably in a desiccator at room temperature in the inert gas atmosphere (argon, nitrogen). Any traces of discoloration may indicate that the drug is decomposing due to its interactions with the polymer and/or the transponder surface. The expected shelf life of the coated transponders is at least 1 year, but the periodical stability testing is recommended. Lower storage temperature (4° C., −20° C. or −70° C.) is also recommended to increase the shelf life of coated transponders.

A protective coating of the same or another polymer (but without the drug) can be applied to prevent the transfer of the drug from one transponder to another. This might be relevant especially if the transponders coated with different drugs are stored in the same container, and are allowed to touch one another.

EXAMPLE 2

Dissolution of the Coating on the Transponders

The dissolution medium is potassium phosphate buffer pH 6.8 (6.5–6.8). The pH needs to be maintained as indicated for a fast dissolution. However, after the dissolution the pH can be adjusted to perform the receptor assay. The dissolution typically takes 10 min to 2 hrs at room temperature, and the exact time needs to be experimentally determined. The temperature can be increased to 40° C. to speed up the dissolution process. A significant factor that affects the process is the amount of polymer in the coating solution; the lesser the amount the faster the dissolution process is.

A reliable indication that the dissolution process is completed is the constancy of the drug concentration in solution. The concentration can be measured using an assay specific for the drug.

EXAMPLE 3

Assay for the inhibition of enzyme activity

The reaction scheme is given in Panel A of FIG. 3. The purpose of the assay is to identify a drug that can inhibit the enzymatic activity of a particular enzyme of pharmaceutical interest. A set of transponders, each coated with a different drug, is used for the assay. The serial number is encoded in the memory of the transponders. The serial number identifies the compound immobilized on the transponder. The transponders are distributed into the wells of a microtiter plate, one transponder per well (96 well plate is suitable), and 100 $\mu$l of the dissolution buffer is added. The transponders are incubated at room temperature for about 2 hours to allow the dissolution of the drug. At this moment, the buffer composition and pH can be adjusted by adding an appropriate amount of a supplemental solution to fit a particular characteristics or a requirement of the enzyme being assayed. The enzyme containing solution is then added to the well, followed by a short incubation period. The substrate for the enzyme is added, and the mixture is incubated for a time sufficient for the development of an observable characteristics of the product of the enzymatic reaction. The substrate can be chromogenic or fluorogenic, in such case the color of fluorescence will be observed, respectively. The well(s) exhibiting a low amount of color or fluorescence, thus indicative of the inhibition of the enzyme by the drug originally immobilized on the transponder, are identified by inspection or by a robotic system. The transponder is pulled out from the well, and its serial number determined on a dedicated scanner. Thus the identified inhibitor of the enzyme can be subjected to further analysis in different assays.

EXAMPLE 4

Receptor-based Assay

The reaction scheme is given in Panel B of FIG. 3. The purpose of the assay is to identify a chemical compound that can bind to a receptor. The compound is fluorescent, as are most other compounds from the library being tested. Wells of a microtiter plate are coated with the receptor. The principle of coating can be hydrophobic interactions, in such case a special microtiter plate is used (Nunc Maxisorb). Alternatively, the principle can be the binding to a receptor-specific antibody previously immobilized on the plate. The coating typically involves a 1 to 16 hour incubation with the receptor at 4° C. Many other methods to immobilize the receptor are possible.

A set of transponders, each coated with a different drug from the library being tested, is used for the assay. The serial number is encoded in the memory of the transponders. The serial number identifies the compound immobilized on the transponder. The transponders are distributed into the wells of a new microtiter plate (96 well plate is suitable), one transponder per well, and 100 $\mu$l of the dissolution buffer is added. The transponders are incubated at room temperature for about 2 hours to allow the dissolution of the drug. At this moment, the buffer composition and pH can be adjusted by adding an appropriate amount of a supplemental solution to fit a particular characteristics or a requirement of the receptor being assayed.

The solution containing the chemical compound is transferred from the microtiter plate containing the transponder to the well precoated with the receptor, and both well numbers are recorded. The compound is allowed to equilibrate with the receptor (typically for 10 min to 2 hr). The wells are washed thoroughly with a buffer, and then the fluorescence of the well is measured on a microtiter plate reader. Fluorescence of the well is indicative of the binding of the compound originally immobilized on the transponder to the receptor. Such wells are identified by inspection or by a robotic system. The transponder is pulled out from the corresponding well, and its serial number is determined on a dedicated scanner. The serial number reveals the identity of the compound from the library and the compound can be subjected to further analysis in different assays.

EXAMPLE 5

Receptor-based Competitive Assay

The reaction scheme is given in Panel C of FIG. 3. The purpose of the assay is to identify a chemical compound that can bind to a receptor. The assay is configured in a competitive mode with a biomolecule that is known to bind to the receptor, but does not possess all the desired pharmacological properties. The binding is the required property of the drug in most cases, but it is not necessary sufficient for the desired pharmacological action of the drug. The biomolecule is a low molecular weight compound which, for the purpose of this example, is labeled with biotin, and the labeling does not significantly affect the binding properties of the compound. The biotin-labeled compound is denoted in Panel C, FIG. 3, as C*.

Wells of a microtiter plate are coated with the receptor. The principle of coating can be hydrophobic interactions, in such case a special microtiter plate is used (Nunc Maxisorb). Alternatively, the principle can be the binding to a receptor-specific antibody previously immobilized on the plate. The coating typically involves a 1 to 16 hour incubation with the receptor at 4° C. Many other methods to immobilize the receptor are possible.

A set of transponders, each coated with a different drug, is used for the assay. The serial number is encoded in the memory of the transponders. The serial number identifies the compound immobilized on the transponder. The transponders are distributed into the wells of a new microtiter plate (96 well plate is suitable), one transponder per well, and 100 $\mu$l of the dissolution buffer is added. The transponders are incubated at room temperature for about 2 hours to allow the dissolution of the drug. At this moment, the buffer composition and pH can be adjusted by adding an appropriate amount of a supplemental solution to fit a particular characteristics or a requirement of the receptor being assayed.

The solution containing the chemical compound is transferred from the microtiter plate containing the transponder to the well precoated with the receptor, and both well numbers are recorded. The compound is allowed to equilibrate with the receptor (typically for 10 min to 2 hr), then the biotin-labeled competing reagent is added, and the mixture is incubated for a time sufficient for the binding of the reagent to the receptor. The wells are washed thoroughly with a buffer, and then HRPO (horse radish peroxidase) labeled streptavidin solution is added to the well. The wells are washed thoroughly again, and a chromogenic or a fluorogenic substrate is added to the well. After a suitable time for the HRPO enzymatic reaction, the absorbance or fluorescence is measured on a microtiter plate reader. No absorbance or fluorescence, respectively, or a low amount of absorbance or fluorescence, in the well is indicative of the binding of the compound originally immobilized on the transponder to the receptor. Such wells are identified by inspection or by a robotic system. The transponder is pulled out from the corresponding well, and its serial number determined on a dedicated scanner. Thus the identified inhibitor of the enzyme can be subjected to further analysis in different assays.

EXAMPLE 6

Fluorescence Polarization Assay

The reaction scheme is given in panel C of FIG. 3. The purpose of the assay is to identify a chemical compound that can bind to a receptor. The assay is analogous to that of Example 5, since the assay is configured in a competitive mode with a biomolecule that is known to bind to the receptor, but does not possess all the desired pharmacological properties. The biomolecule is a low molecular weight reagent (hapten) which, in this example, is haptenated with fluorescein (to form a fluorescein-hapten conjugate, denoted as C* in Panel C of FIG. 3). The labeling should not significantly affect the binding properties of the reagent. The assay is done on a fluorometer, in which the excitation light needs to be polarized, and the instrument needs to be capable of measuring the polarization signal. The objective of the assay is to detect changes of the polarization signal from the fluorescein-hapten conjugate bound to the receptor after the dissolution of the chemical compound being tested.

A set of transponders, each coated with a different chemical compound, is used for the assay. The serial number is encoded in the memory of the transponders. The serial number identifies the compound immobilized on the transponder. The required amount of the soluble receptor and the fluorescein conjugate is added to the wells of a microtiter plate, or any other convenient vessel. The buffer is formulated in such a way that after the dissolution of the coating on the transponders the buffer is suitable for the analysis of the binding of the chemical compounds to the receptor. The amount of the fluorescein conjugate is adjusted to assure the equilibrium with the receptor in which a substantial amount of the conjugate is bound to the receptor. This will provide a substantial basal signal of emitted polarized light.

The transponders are added to the wells of the microtiter plate, one transponder per each well. The coating undergoes a dissolution process, and the chemical compound is slowly released to the buffer which contains the receptor. Biologically active compounds will compete with the conjugate for the occupancy of the binding site on the receptor, reducing the amount of the fluorescein conjugate bound to the receptor, thus reducing the polarization signal. The well(s) exhibiting a reduced polarization signal are identified by inspection or by a robotic system. The transponder is pulled out from the corresponding well, and its serial number determined on a dedicated scanner. Thus the identified chemical compound can be subjected to further analysis in different assays.

The assay enables the kinetic mode of the analysis in which the fluorescence in the well is monitored periodically after the coated transponder is added to the well, providing the investigator with the dependence of the polarization signal on the concentration of the chemical compound, thus potentially increasing the accuracy of the assay.

EXAMPLE 7

Attenuation of Bacterial Growth

In a modified form of the assay, separate vessels for individual transponders are not needed. Let's consider a screen for new antibiotics as an example. The compounds from a large chemical library are coated on the transponders. The transponders are added to the suspension of the target microorganism in a nutrient medium prepared with agar, and the whole mixture is poured as a thin layer on a surface (e.g. Petri dish). Agar solidifies, and the coating of the transponders is dissolved and the compounds are released into the vicinity of the transponder. If the compound has antimicrobial properties, upon prolonged incubation at a temperature permissive for growth of a given microorganism, a zone of no growth around the transponder will be seen. The transponder from the no-growth zone is picked from the surface and decoded electronically. The compound having the anti-microbial properties is identified from the decoded serial number.

It is important in this application to control for the time needed to release the drug from the coating on the transponders. It is desirable that this drug release time is comparable to the time needed for the bacterial growth to appear in agar or on the surface of agar.

EXAMPLE 8

High-throughput Assay with Fluorescein-labeled Receptor

The reaction scheme is given in panel D of FIG. 3. This assay takes advantage of a property of surfaces coated with the mixture of the polymer and the relevant chemical compound, such property being the display of the chemical compound on the surface as a result of its entrapment in the polymer coating despite the lack of the covalent chemical bond between the compound and either the surface itself or the polymer.

The receptor is labeled with fluorescein. The labeling should be done such as to yield a moderate number of the conjugated fluorescein molecules per one receptor molecule. Thus the labeling should not significantly change the binding properties of the receptor. The labeled receptor is incubated with a set of the transponders coated with different chemical compounds for a short period of time, but sufficient for the dissolution of a small fraction of the chemical compound in the coating of the transponder. The bulk of the chemical compound will be still entrapped in the coating on the transponder. If the transponder carries a chemical compound that is able to bind to the receptor, some of the receptor molecules will bind to the surface of the transponder by virtue of interacting with the chemical compound on the surface of the transponder. The transponders are quickly washed, and the fluorescence emitted by the transponder's surface is analyzed, followed by the decoding of the serial number.

The assay can be performed in a high throughput mode on a modified flow cytometer. The modification involves the placement of a radio frequency antenna in the proximity of the flow chamber to allow the decoding of a serial number of the transponder passing through the chamber and associating the serial number with the fluorescence emitted by the surface of the transponder.

EXAMPLE 9

Use of an Alternative Tag in the Receptor Assay

In this assay, transponders are not used. Instead, small solid phase particles made of silicon, and having the index numbers etched on their surfaces, are implemented.

The silicon particles are coated with the mixture of the chemical compound and the polymer as described in Example 1. All particles having one index number encoded on the surface of silicon are coated with the same chemical compound. Thus the index number unequivocally identifies the chemical compound deposited on the particle.

The assay is similar to that of Example 3. The purpose of the assay is to identify a drug that can inhibit the enzymatic activity of a particular enzyme of pharmaceutical interest. A set of solid phase particles, each coated with a different drug, is used for the assay. The particles are distributed into the wells of a microtiter plate (96 well plate is suitable), and 100 $\mu$l of the dissolution buffer is added. The particles are incubated at room temperature for 2 hours to allow the dissolution of the drug. At this moment, the buffer composition and pH can be adjusted by adding an appropriate amount of a supplemental solution to fit a particular characteristics or a requirement of the enzyme being assayed. The enzyme containing solution is then added to the well, followed by a short incubation period. The substrate for the enzyme is added, and the mixture is incubated for a time sufficient for the development of an observable characteristics of the product of the enzymatic reaction. The substrate can be chromogenic or fluorogenic, in such case the color of fluorescence will be observed, respectively. The well(s) exhibiting a low amount of color or fluorescence, thus indicative of the inhibition of the enzyme by the drug originally immobilized on the particle, are identified by inspection or by a robotic system. The particle is pulled out from the well, and its index number etched on the surface determined using a optical microscope after the polymer coating is removed as a result of a prolonged incubation in the dissolution buffer at an elevated temperature. Thus the inhibitor of the enzyme is identified from the index number, and the inhibitor can be subjected to further analysis in different assays.

I claim:

1. A method of screening for a chemical compound with a pharmaceutically useful property comprising the steps of:
   (a) providing a solid phase particle having:
      (i) a chemical compound associated with the solid phase particle, such association not involving a covalent bond between the chemical compound and the solid phase particle or its part, and
      (ii) a tag identifying the chemical compound associated with the solid phase;
   (b) adding the solid phase particle to a bioassay liquid medium;
   (c) causing the dissolution of at least a part of the chemical compound associated with the solid phase particle;
   (d) performing a bioassay on the bioassay liquid medium containing the chemical compound;
   (e) identifying a chemical compound with a pharmaceutically useful property comprising the steps of:
      (i) identifying the solid phase particle associated with the chemical compound with the pharmaceutically useful property, and
      (ii) determining the identity of the chemical compound with the pharmaceutically useful property by reading the tag.

2. The method of claim 1 wherein:
   (a) the tag identifying the compound is a transponder, said transponder having a serial number encoded in it; and
   (b) reading the tag involves decoding the serial number of the transponder.

3. A method of coating the solid phase particle of claim 1 with a chemical compound, comprising the steps of:
   (a) preparing the mixture of the chemical compound and a polymer in a solvent;
   (b) coating the said solid phase particle by immersing and incubating the transponders in the said mixture;
   (c) drying the solvent off.

4. The method of claim 3 wherein the solid phase particle is a transponder.

5. The method of claim 1 wherein the solid phase particle is associated with more than one chemical compound, and the decoding identifies a group of more than one chemical compounds.

6. The solid phase particle, comprising:
(i) a chemical compound associated with the solid phase particle, such association not involving a covalent bond between the chemical compound and the solid phase particle or its part, and
(ii) a transponder, said transponder having a serial number encoded in it, such serial number identifying the chemical compound associated with the solid phase.

7. A chemical compound identified through the use of an assay of claim 1.

8. The method of claim 1, wherein the dissolution occurs in less than 2 hours.

9. The method of claim 1, wherein the solid phase particle is coated with a coating comprising the chemical compound and a soluble polymer.

10. The method of claim 9, wherein the soluble polymer is selected from the group consisting of poly-lactic acid, alginic acid, cellulose, polyacrylamide, and an acrylic acid/acrylic anhydride copolymer.

* * * * *

UNITED STATES PATENT AND TRADEMARK OFFICE
CERTIFICATE OF CORRECTION

PATENT NO. : 5,981,166
DATED : November 9, 1999
INVENTOR(S) : Wlodek Mandecki

It is certified that error appears in the above-identified patent and that said Letters Patent is hereby corrected as shown below:

On the title page:

In [75] Inventor: Change "Edison, N.J." to -- Princeton, Jct., N.J. --

In [56] Other Publications:

Albertsen - change "Isolation" to -- isolation --

Alper - change "Discovery" to -- discovery --

Under U.S. Patent Documents:

Drmanac, R. et al. - change "largescale" to -- large-scale --

Gingeras TR et al. - change "immobolized" to -- immobilized--

Maskos - change "E." to -- U.--;
       change "hybridisations [sic]" to -- hybridizations-- throughout reference.

McHugh, T. - change "Microsphere Immunoassay for the Quantitative and Simultaneous Detection of Multiple Soluble Analytes" to --microsphere immunoassay for the quantitatve and simultaneous detection of multiple soluble analytes--

UNITED STATES PATENT AND TRADEMARK OFFICE
CERTIFICATE OF CORRECTION

PATENT NO. : 5,981,166
DATED : November 9, 1999
INVENTOR(S) : Wlodek Mandecki

Page 2 of 8

It is certified that error appears in the above-identified patent and that said Letters Patent is hereby corrected as shown below:

Under U.S. Patent Documents:

Principles and Practice of Immunoassay (1994) - change "Design and Optimization" to -- design and optimization --

Principles and Practice of Immunoassay (1995) - change "Fluoroimmunoassay" to -- fluoroimmunoassay --

Sambrook, B.S. - change "Cloning" to -- cloning --

Col. 1, Line 9 - change "and more specifically" to -- and, more specifically,--

Col. 1, Line 21 - change "years" to --years,--

Col. 1, Line 32, change "create" to -- creates--

Col. 1, Line 57 - change "i.e." to --i.e.,--

Col. 1, Line 62 - change "i.e." to --i.e.,--

UNITED STATES PATENT AND TRADEMARK OFFICE
CERTIFICATE OF CORRECTION

PATENT NO. : 5,981,166
DATED : November 9, 1999
INVENTOR(S) : Wlodek Mandecki

It is certified that error appears in the above-identified patent and that said Letters Patent is hereby corrected as shown below:

Col. 2, Line 13 change "includes" to --also includes--

Col. 2, Line 14 delete "also"

Col. 2, Line 38 change "application" to --applications,--

Col. 2, Line 61 delete "," after the word vessel and insert --,-- after the word performed Col. 3, Line 6 - insert --,-- after the word positive Col. 3, Line 7 - insert --,-- after the word receptor Col. 3, Line 8, delete "," after the word vessels Col. 3, Line 22 - change "transponders, and" to --transponders and,--

Col. 4, Line 18 change "a" to --the--

UNITED STATES PATENT AND TRADEMARK OFFICE
CERTIFICATE OF CORRECTION

PATENT NO. : 5,981,166
DATED : November 9, 1999
INVENTOR(S) : Wlodek Mandecki

It is certified that error appears in the above-identified patent and that said Letters Patent is hereby corrected as shown below:

Col. 4, Line 34 delete "of"

Col. 4, Line 54 change "a form" to --the form--

Col. 5, Line 4 delete "Design of the Laser-Induced Transponder"

Col. 5, Line 7 change "i.e." to --i.e.,--

Col. 5, Line 48 change "feasible, including" to --feasible including,--

Col. 5, Line 49 insert --,-- after the word "to"

Col. 6, Line 10 delete "Coating Procedure"

Col. 6, Line 41 insert --,-- after the word "daltons"

UNITED STATES PATENT AND TRADEMARK OFFICE
CERTIFICATE OF CORRECTION

PATENT NO. : 5,981,166
DATED : November 9, 1999
INVENTOR(S) : Wlodek Mandecki

Page 5 of 8

It is certified that error appears in the above-identified patent and that said Letters Patent is hereby corrected as shown below:

Col. 8, Line 22 insert --,-- after the word dried

Col. 8, Line 23 insert --,-- after the word chloroform

Col. 8, Line 23 change "coating (if" to --coating. (If--

Col. 8, Line 38 insert --,-- after the word stirred

Col. 8, Line 38 insert --,-- after the word motor

Col. 8, Line 59 change "mechanisms are" to --mechanism is--

Col. 9, Line 3 insert --of-- after the word use

Col. 9, Line 5 change "one to" to --to one--

Col. 9, Line 6 change "Then" to --Then,--

Col. 9, Line 14 change "beaker moved" to --beaker are moved--

Col. 9, Line 21 change "needed to --needed,--

Col. 9, Line 22 change "cases" to --cases,--

UNITED STATES PATENT AND TRADEMARK OFFICE
CERTIFICATE OF CORRECTION

PATENT NO. : 5,981,166
DATED : November 9, 1999
INVENTOR(S) : Wlodek Mandecki

It is certified that error appears in the above-identified patent and that said Letters Patent is hereby corrected as shown below:

Col. 9, Line 31 delete "the" after the word "but"

Col. 9, Line 33 change "(4°C., -20°C. or -70°C.)" to --(4°C -20°C or -70°C)--

Col. 9, Line 39 insert --,-- after the word relevant

Col. 9, Line 47 change "maintained as indicated" to --maintained, as indicated,--

Col. 9, Line 48 change "dissolution" to --dissolution,--

Col. 9, Line 52 change "40°C." to --40°C--

Col. 9, Line 55 change "amount" to --amount,--

Col. 10, Line 11 change "characteristics" to --characteristic--

Col. 10, Line 16 change "characteristics" to --characteristic--

Col. 10, Line 24 change "Thus" to --Thus,--

UNITED STATES PATENT AND TRADEMARK OFFICE
CERTIFICATE OF CORRECTION

PATENT NO. : 5,981,166
DATED : November 9, 1999
INVENTOR(S) : Wlodek Mandecki

It is certified that error appears in the above-identified patent and that said Letters Patent is hereby corrected as shown below:

Col. 11, Line 13 change "necessary" to --necessarily--

Col. 11, Line 22 change "case" to --case,--

Col. 11, Lines 38-39 change ""characteristics" to --characteristic--

Col. 11, Line 60 change "Thus" to --Thus,--

Col. 12, Line 23 change "that" to --that,--

Col. 12, Line 24 change "transponders" to --transponders,--

Col. 12, line 42 change "Thus" to --Thus,--

Col. 12, Line 49 change "thus" to --thus,--

Col. 12, Line 57 change "antibiotics" to --antibiotics,--

UNITED STATES PATENT AND TRADEMARK OFFICE
CERTIFICATE OF CORRECTION

PATENT NO. : 5,981,166
DATED : November 9, 1999
INVENTOR(S) : Wlodek Mandecki

It is certified that error appears in the above-identified patent and that said Letters Patent is hereby corrected as shown below:

Col. 12, Line 62 change "solidifies and" to --solidifies,--

Col. 12, Line 63 change "dissolved" to --dissolved,--

Col. 13, Line 26 change "Thus" to --Thus,--

Col. 13, Line 32 change "be still" to --still be--

Col. 13, Line 60 change "Thus" to --Thus,--

Col. 14, Lines 6 change "characteristics" to --characteristic--

Col. 14, Lines 11 change "characteristics" to --characteristic--

Col. 14, Line 20 change "Thus" to --Thus,--

Signed and Sealed this

Twenty-eighth Day of November, 2000

Attest:

Q. TODD DICKINSON

Attesting Officer

Director of Patents and Trademarks